(12) United States Patent
Wang et al.

(10) Patent No.: US 6,284,333 B1
(45) Date of Patent: *Sep. 4, 2001

(54) MEDICAL DEVICES MADE FROM POLYMER BLENDS CONTAINING LOW MELTING TEMPERATURE LIQUID CRYSTAL POLYMERS

(75) Inventors: Lixiao Wang, Maple Grove; Jianhua Chen, Plymouth, both of MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/257,677

(22) Filed: Feb. 25, 1999

Related U.S. Application Data

(63) Continuation-in-part of application No. 08/926,905, filed on Sep. 10, 1997.

(51) Int. Cl.$^7$ ............ B29D 22/02; B29D 23/00; B32B 25/02
(52) U.S. Cl. ............ 428/35.5; 428/36.8; 428/36.92; 604/95.01; 604/96.01; 604/103.06; 604/288.01
(58) Field of Search ............ 428/35.2, 35.5, 428/35.7, 36.9, 36.92, 480, 483, 500, 1.33, 1.25, 36.8; 525/64, 66, 179, 166; 604/96.01, 95.01, 103.06, 288.01

(56) References Cited

U.S. PATENT DOCUMENTS

| Re. 32,983 | 7/1989 | Levy | 428/36.92 |
|---|---|---|---|
| 3,991,014 | 11/1976 | Kleinschuster | 260/47 |
| 4,067,852 | 1/1978 | Calundann | 260/47 |
| 4,083,829 | 4/1978 | Calundann et al. | 260/47 |
| 4,130,545 | 12/1978 | Calundann | 260/40 |
| 4,154,244 | 5/1979 | Becker | 128/349 |
| 4,161,470 | 7/1979 | Calundann | 260/40 |

(List continued on next page.)

FOREIGN PATENT DOCUMENTS

| 0 369 734 | 5/1990 | (EP) | C08L/67/02 |
|---|---|---|---|
| 0 448 886 A1 | 12/1990 | (EP) | |
| 92/19316 | 11/1992 | (WO) | |
| 93/24574 | 9/1993 | (WO) | C08L/101/00 |
| 95/23619 | 9/1995 | (WO) | A61K/29/00 |
| 96/00752 | 1/1996 | (WO) | C08L/67/02 |
| 96/04951 | 2/1996 | (WO) | A61M/25/00 |

OTHER PUBLICATIONS

Polymer Science Dictionary, Second Edition, Edited by Marc Alger, p. 292, Jan. 1997.*

J. P. deSouza et al., "Processing Studies of In Situ Composites Based on Blends of Liquid Crystalline Polymers With Engineering Thermoplastics", *Polymer Preprints*, 392–393 Apr. 1992.

Q. Lin and A.F. Yee, Measurement of Molecular Orientation of Liquid Crystalline Polymer in situ Composites by X–Ray Scattering Technique, *Polymer Preprints*, pp. 298–299, Apr. 1992.

(List continued on next page.)

Primary Examiner—Harold Pyon
Assistant Examiner—Sandra Nolan
(74) Attorney, Agent, or Firm—Vidas, Arrett & Steinkraus

(57) ABSTRACT

A medical device, at least a portion of which is composed of a polymeric material in which the polymeric material is a melt blend product of at least two different thermoplastic polymers, one of the thermoplastic polymers being a thermoplastic liquid crystal polymer (LCP) having a melting point of less than 250° C. The portion of the device made from the melt blend may be a catheter body segment or a balloon for a catheter. The LCP blends suitably also include a non-LCP base polymer having a melting point in the range of about 140° C. to about 265° C.

5 Claims, 1 Drawing Sheet

U.S. PATENT DOCUMENTS

| | | | |
|---|---|---|---|
| 4,318,842 | 3/1982 | East et al. | 524/605 |
| 4,331,786 | 5/1982 | Foy et al. | 525/408 |
| 4,386,174 | 5/1983 | Cogswell et al. | 524/27 |
| 4,433,083 | 2/1984 | Cogswell et al. | 524/27 |
| 4,438,236 | 3/1984 | Cogswell et al. | 525/165 |
| 4,444,817 * | 4/1984 | Subramanian | 428/36 |
| 4,468,364 | 8/1984 | Ide | 264/176 |
| 4,963,313 | 10/1990 | Noddin et al. | 264/573 |
| 5,195,969 | 3/1993 | Wang et al. | 604/96 |
| 5,248,305 * | 9/1993 | Zdrahala | 604/280 |
| 5,264,260 | 11/1993 | Saab | 428/35.5 |
| 5,270,086 | 12/1993 | Hamlin | 428/35.2 |
| 5,290,306 | 3/1994 | Trotta et al. | 606/194 |
| 5,304,340 | 4/1994 | Downey | 264/521 |
| 5,306,246 | 4/1994 | Sahatjian et al. | 604/96 |
| 5,328,468 | 7/1994 | Kaneko et al. | 604/96 |
| 5,330,428 | 7/1994 | Wang | 604/96 |
| 5,348,538 | 9/1994 | Wang et al. | 604/96 |
| 5,358,486 | 10/1994 | Saab | 604/96 |
| 5,447,497 | 9/1995 | Sogard et al. | 604/101 |
| 5,512,051 | 4/1996 | Wang et al. | 604/96 |
| 5,554,120 | 9/1996 | Chen et al. | 604/96 |
| 5,556,383 | 9/1996 | Wang et al. | 604/96 |
| 5,565,530 | 10/1996 | Hattori et al. | 525/419 |
| 5,587,125 | 12/1996 | Roychowdhury | 264/515 |

OTHER PUBLICATIONS

J. M.Schultz, "Structure Evolution in PET Fibers", *Polymer Preprints*, 304–306 Apr. 1992.

J. Liu et al., "Crystal Structure and Transitions in Rigid Rod Thermotropic Liquid Crystal Polymers", *Polymer Preprints*, 337–338 Apr. 1992.

W.J. Farrissey and T.M. Shah, Polyamide Thermoplastic Elastomers, in Handbook of Thermoplastic Elastomers, B.M. Walker and C.R. Rader, eds., pp. 258–281.

B. N. Epstein et al., "Polymer Blends—An Overview", *Polymer Preprints*, 42–43, Jun. 1991.

M.M. Coleman et al., "Miscibility Maps for Copolymer–Copolymer Blends: A Comparison of Theoretical Predictions to Experimental Data", *Polymer Preprints*, 44–45, Jun. 1991.

W.M. Cheng et al., "Main Chain–Side Chain Liquid Crystal Polymer Blends for Improived Physical Properties", *Polymer Preprints*, 50–51, Jun. 1991.

R.R. Matheson, Jr., "Polymers, Processes and Additives as Systems", *Polymer Preprints*, 52–53, Jun. 1991.

S. Allen et al., "The Effect of Additives on Tensile Properties of PPD–T Fibers", *Polymer Preprints*, 54–55, Jun. 1991.

J.R. Runt et al., "Phase Behavior and Crystallization in Blends of Poly(butyleneterephthalate) and Polyarylate", *Polymer Preprints*, 56–57, Jun. 1991.

T.W. Cheng et al., "Property and Morphology Relationships for Ternary Blends of Polycarbonate, Brittle Polymers, and an Impact Modifier", *Polymer Preprints*, 58–59, Jun. 1991.

M.M. Nir and R.E. Cohen, "Compatibilization of Blends of Crystallizable Polybutadiene Isomers by Precipitation and by Addition of Amorphous Diblock Copolymer", *Polymer Preprints*, 60–61, Jun. 1991.

U. M. Vakil and G.C. Martin, "Analysis of Structure–Property Relations in Crosslinked Epoxies", *Polymer Preprints*, 62–63, Jun. 1991.

Superex Polymer, Inc. press release, "Dual Compatibilized Recyclable PET–LCP Alloys with Enhanced Barrier and Structural Performance".

Hoechst Celanese Vectra ® Liquid Crystal Polymer Product Information.

Superex Polymer, Inc Advertisement, "Building product value through new processing and application technologies".

Xydar® product data, Sep. 1994.

Amoco Engineering Plastics for Performance and Value product brochure.

B. Miller, "Rotating Dies Pave Way for Extruding LCP", Plastics World.

A.M. Adur and L.J. Bonis, "PET–LCP Compatibilized Alloys: A New Unique Development".

G.C. Rutledge, "Modelling Chain Rigidity and Orientation in Liquid Crystalline Polymers", *Polymer Preprints*, 537–538 Apr. 1992.

R.K. Menon, "Kinetic Theory for Liquid Crystalline Polymer Solutions", *Polymer Preprints*, 574–575 Apr. 1992.

O.V. Noah and N.A. Plate, "Simulation of Macromolecules Conformations in Processes of Intra– and Intermolecular Crosslinking", *Polymer Preprints*, 578–579 Apr. 1992.

H. Boublil et al., "Morphology of Polyamide and Polyether Block Amide Blends", *Polymer Engineering and Science*, vol. 29, No. 10, 679–684, May 1989.

E. Okoroafor and J. Rault, "Cryodilation of Thermoplastic PEBA Elastomers", *J. Polymer Sci: Part B: Polymer Physics*, Vopl. 29, 1427–1436, 1991.

E. Barmatov et al., "Oriented Networks of Comb–Shaped Liquid Crystalline Polymers", *Polymer Preprints*, 706–707, Aug. 1993.

M. Brehmer et al., "LC–Elastomers by Chemical and Physical Crosslinking", *Polymer Preprints*, 708–709, Aug. 1993.

A.Y. Bilibin and A.R. Stepanova, "Synthesis of Liquid Crystalline Multiblock Copolymers With Definite Structure of Rigid Block", *Polymer Preprints*, 714–715, Aug. 1993.

Y. Yang et al., Orientation and Strain–Induced Liquid–Crystalline Phase Transition of Networks of Semi–Rigid Chains, *Polymer Preprints*, 729–730, Aug. 1993.

R. Stadler and T. Oehmichen, "Telechelic Oligoaramides—A Means for Rigid–Rod Molecular Inforcement of Thermoplastic Materials", *Polymer Preprints*, 731–733, Aug. 1993.

D.H. Weinkauf and D.R. Paul, "The Influence of Molecular Architecture on Gas Transport Properties of Liquid Crystalline Polymers", *Polymer Preprints*, 372–373, Aug. 1991.

P. A. Rodgers and I.C. Sanchez, "Gas Solubility in Polymers and Blends", *Polymers Preprints*, 392–393, Aug. 1991.

W. Brostow, "Properties of Polymer Liquid Crystals: Choosing Molecular Structures and Blending", *Polymer*, vol. 31, 979–995, Jun. 1990.

R. J. Lewis, Sr., "Hawley's Condensed Chemical Dictionary, 12th ed.", pp. 704, 932–934, 936–939, (1993).

Kirk–Othmer Concise Encyclopedia of Chemical Technology, pp. 148–149, 391–395, 814–819, 924–939 (1985).

P. Peyser, "Glass Transition Temperatures of Polymers" in Polymer Handbook 3rd ed. J. Brandrup and E.H. Immergut eds., VI–258–259.

P.J. Collings, "Liquid Crystals, Nature's Delicate Phase of Matter", pp. 20–23, 162–180 (1990).

I.C. Khoo, "Liquid Crystals Physical Properties and Nonlinear Optical Phenomena", p. 5–11, 1995.

* cited by examiner

MEDICAL DEVICES MADE FROM POLYMER BLENDS CONTAINING LOW MELTING TEMPERATURE LIQUID CRYSTAL POLYMERS

CROSS REFERENCE TO RELATED APPLICATION

This application is a continuation-in-part of copending and commonly owned U.S. application Ser. No. 08/926,905, filed Sep. 10, 1997, pending, incorporated herein by reference in its entirety.

BACKGROUND OF THE INVENTION

In copending U.S. application Ser. No. 08/926,905 (corresponding to PCT/US98/18345 filed Sep. 4, 1998) there are described medical balloons made from liquid crystal polymer blends. The blends comprise polymer melt blend product of a) a thermotropic main-chain liquid crystal polymer (LCP);

b) a crystallizable thermoplastic polymer; and c) at least one compatibilizer for a) and b).

The melt blend balloons so produced have very high strength, but have relatively low compliance and flexibility.

The practice of the invention of application Ser. No. 08/926,905, however, has been limited in that the thermoplastic polymer was a material with a relatively high melting temperature, such as crystallizable polyester or polyamide polymers. The known LCPs had melting points above 275° C., thus requiring that the thermoplastic polymer be stable at temperatures near or above the LCP melting temperature in order to process the melt blend.

Many thermoplastic polymers have higher flexibility and elasticity than polyesters or polyamides but their melting points have been too low to be processable in melt blends with LCPs.

Recently LCPs with melting points below 250° C. have been prepared and commercialized. The inventors of the present invention have now discovered a much wider range of thermoplastic polymers can be blended with such low melting temperature LCPs to produce blend materials useful in fabricating medical devices.

SUMMARY OF THE INVENTION

In one aspect the invention comprises a medical device at least a portion of which is composed of a polymeric material in which the polymeric material is a melt blend product of at least two different thermoplastic polymers, one of the thermoplastic polymers being a thermoplastic liquid crystal polymer having a melting point of about 275° C. or less, and especially 250° C. or less. Catheters and catheter balloons are specific medical devices to which the invention may be applied.

The low temperature LCP component may be used at relatively low levels to impart higher strength and resistance to shrinkage to base polymer materials of greater flexibility, softness or elasticity than had previously been usable with available LCPs.

DETAILED DESCRIPTION OF THE INVENTION

Figure 1:
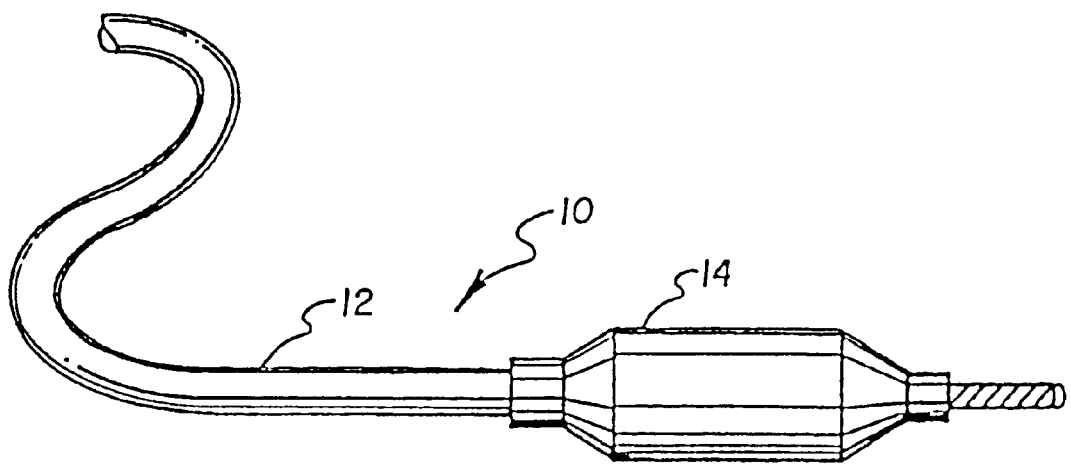
FIG. 1 is a perspective fragmentary view of a balloon catheter embodiment of the present invention.

The blend products used in the present invention include a thermoplastic non-LCP base polymer in an amount of from about 50 to about 99.9% by weight, preferably from about 85 to about 99.5 percent. The blend products also include from about 0.1 to about 20 weight percent, more preferably from about 0.5 to about 15 percent, of a liquid crystal polymer having a melting point of less than 275° C., preferably less than 250° C. A melt compatibilizer, such as disclosed in application Ser. No. 08/926,905, may also be employed in an amount of from 0 to about 30 weight percent.

The base polymer should have a melting point within about 70° C., preferably within about 50° C. and more preferably within about 35° C. of the liquid crystal polymer component. Suitably the base polymer has a melting point in the range of from about 140° C. to about 265° C., preferably about 220° C. or less, and more preferably from about 150° C. to about 210° C. Depending on the liquid crystal polymer melting temperature, the base polymer may be for instance an acetal homopolymer or copolymer (typical mp 160–185° C.); cellulosic polymers (mp. 140–190° C.); poly (chlorotrifluoroethylene) (mp. 200–220); poly(vinylidine fluoride) (mp 155–180° C.); nylon 6,6 (mp. 250–260); nylon 6 (mp 215–225); nylon 6,10 (mp 210–220); nylon 12 (mp 170–180); nylon 11 (mp 180–190); polyoxymethylene (mp 165–185); higher melting grades of poly(methyl methacrylate) (e.g. mp 140–160° C.); polypropylene homopolymers and copolymers (mp 160–175); polycarbonate polymers and copolymers (mp 220–230° C.); poly (ethylene-vinyl alcohol) (mp 140–180); polyethylene terephthalate; polybutylene terephthalate; polytrimethylene terephthalate; thermoplastic polyurethanes (aromatic and/or aliphatic); thermoplastic elastomers such as polyester elastomers sold under the tradenames Hytrel® and Arnitel®, polyamide elastomers sold under the tradename Pebax®, and thermoplastic polyurethane elastomers sold under the tradename Pellethane®. Particularly preferred base polymer materials include Pebax® 7033 (mp 174° C.) and 7233 (mp 175° C.), sold by Atochem North America, and Arnitel EM 740 (mp 221° C.), sold by DSM Engineering Plastics.

Use of some of these base polymers in LCP blends has been described in the prior application Ser. No. 08/926,905, for instance PET/LCP blends. However, by using lower melting temperature LCPs, as described herein, processing is made easier. For instance, where there is a large temperature difference between the base polymer and the LCP component, a dual extruder may have had to be used to allow the polymers to be separately melted before they could be mixed. With a smaller difference in melt temperatures the melt blend of LCP and base polymer can be prepared by melting a dry blend of the two polymers, or one of the two polymers in solid form may be added to a melt of the other, without substantial polymer degradation. A dual extruder technique can still be used to obtain blends with base polymers whose melt temperature is substantially lower than that of the LCP used in the present invention. Therefore the range of usable base polymers is substantially increased in the present invention over those of prior application Ser. No. 08/926,905.

The LCP used in the invention hereof is one characterized by a melting point below 275° C., preferably below 250° C., suitably in the range of 150–249° C., and even more preferably about 230° C. or less. The LCP is suitably a thermotropic liquid crystal polymer. Specific such LCPs include Vectra® LKX 1107, a polyester-type liquid crystal polymer (mp 220° C.), and Vectra® LKX 1111, a polyesteramide-type liquid crystal polymer (mp. 220° C.), both sold by Ticona, a Hoechst company.

Compatibilizers also may be used in the melt blend composition. The compatibilizer may be for instance a block copolymer comprising a block which is structurally similar or otherwise is soluble in the base polymer and a block which is structurally similar or otherwise soluble with the LCP. Compatibilizers may be necessary if phase separation of the blend in the melt phase is a problem. However, phase separation of the solid phase melt blend product is not necessarily a reason to employ a compatibilizer. Solid phase separation may enhance the reinforcing effect of the LCP component. Optical clarity, however, is lost with phase separation in the solid phase. Use of a compatibilizer may be useful if optical clarity is a desired objective or where it is desired to improve adhesion between LCP fiber and the base polymer.

The blend materials described herein are particularly suited for use in forming dilatation and/or stent placement catheters or balloons thereon. Such catheters are used for percutaneous transluminal angioplasty and other minimally invasive procedures. Use in forming a proximal or intermediate portion of the catheter body may reduce or eliminate the need for braid or other physical reinforcement so that a reduced profile may be provided.

A particularly preferred use of the melt blend materials described herein is as a material for a catheter balloon. The balloon diameter may be from about 1.5 to about 30 mm, depending on the application to which it is put, and are suitably formed to provide a double wall thickness, measured on the uninflated collapsed balloon, of about 0.0002"–0.0020".

The balloons of the invention may be either single layer balloons, or multilayer balloons.

Referring to the drawing, there is shown in FIG. 1 a catheter 10 comprising an elongated flexible tube 12 with a balloon 14, made of an LCP reinforced polymer blend in accordance with the invention hereof, mounted at the distal end thereof. A portion of tube 12 also may be formed from an LCP reinforced polymer blend, which may be the same or different from the blend used to form the balloon.

Balloon formation may be begun by extruding a tube from a melt of the polymer blend material. Some initial orientation of the LCP occurs as the blend material is drawn down during the extrusion process. This process is typically known as machine orientation and is in the direction of the extrusion operation. Orientation which occurs during the extrusion process is desirable as it induces formation of fiber form LCP in the tubing so-formed. Orientation can be enhanced by increasing extrudate puller speed. Also, if an angled fiber morphology is desired, a counter-rotating die and mandrel system can be used in the extrusion.

Following extrusion, the extruded tube optionally may be conditioned at 20–30° C. at a controlled humidity in the range of 10–50% for a period of at least 24 hours. This conditioning provides a constant low moisture level in the tube which prevents hydrolysis and helps to optimize the orientation of the polymer in the subsequent blowing steps.

Balloon blowing may follow conventional single or multi-step techniques known in the art, for instance free blowing, mold blowing, or a combination of both, optionally with a preceding axial stretching step. The axial stretch ratio, if used, is suitably from about 2× to about 5×. Balloon forming will typically be performed at a temperature in the range of 95° C. to 165° C., depending on the base polymer material and the amount of LCP incorporated into the blend. The balloon forming step should be performed above the glass transition temperature but below the melt temperature of the base polymer material (for block copolymers the blowing temperature should be above the highest glass transition). The radial expansion ratio is suitably from about 3× to about 12×. Depending on the technique, expansion pressures may range from about 200–500 psi (1379–3447 kPa).

In some cases it may be desirable to subject the formed balloon to a heat set step. In this step the pressurized balloon is held for a brief time, suitably about 5–60 seconds, at a temperature above that used to form the balloon after which the mold is rapidly quenched to ambient temperature and the balloon removed from the mold.

In the absence of a compatibilizer, or where the compatibilizer is only effective to compatibilize the melt, the LC and base polymers will typically undergo phase separation on cooling so that an opaque article is obtained. The phase separation, however, occurs on a microscopic scale so that the LC discontinuous phase is uniformly distributed in a continuous base polymer phase. The LC discontinuous phase is fibrous, and the fibers orient during the stretching and blowing steps of the balloon formation so a high level of reinforcement is provided to the base polymer. However, reinforcement by the fibrous LC phase can be achieved without a major reduction in flexibility and without presenting huge increases in melt viscosity, both of which effects are commonly encountered when reinforcing fillers are added to thermoplastic polymer compositions. Moreover, the fiber size is so small that, even with the extremely thin films encountered in angioplasty balloons, film porosity is not created.

The invention is illustrated by the following non-limiting examples.

EXAMPLES

Example 1

Pebax 7033 polymer was melt blended at a temperature of 225° C. with liquid crystal polymer Vectra LKX 1107 at the ratio of 95% to 5% respectively by weight and the mixture was extruded into tubing of 0.018×0.037 inch (0.48×0.94 mm). A 3.0 mm balloon was formed from the tube at 98° C. and at 450 psi (4102 kPa) forming pressure using a 3.0 mm mold form in a single blowing step. The balloon had a double wall thickness of 0.00175 inch (0.044 mm) and had an opaque appearance. The balloon burst at 265 psi (1827 kPa). This reinforced composite balloon has much higher puncture resistance and more durability than a similar balloon made from 100% Pebax 7033.

Improved length stability upon expansion is a desirable property for high strength, relatively compliant balloons used for stent deployment. The following Examples 2 and 3 demonstrate that the LCP blends used in the invention provide improvement is length stability for such balloons.

Example 2

The same composition as shown in Example 1 was used to extrude a tube of 0.022×0.036 inch (0.56×0.91 mm). The 3.0 mm balloon was made at 95° C. with a blowing pressure of 400 psi (2758 kPa). The balloon with double wall thickness of 0.0014 inch (0.036 mm) was inflated from 4 atm (405 kPa) to 13 atm (1317 kPa) at 1 atm (101 kPa) increments and the balloon length change was 2.5% at the span of 4–13 atm.

For comparison 100% Pebax 7033 tubing with dimension of 0.0192×0.0344 (0.49–0.87 mm) was used to form 3.0 mm balloon at 95° C. and 400 psi (2758 kPa) blowing pressure. The formed balloon with double wall thickness of 0.0014 inch (0.036 mm) was inflated from 4 atm (405 kPa) to 13 atm (1317 kPa) at 1 atm (101 kPa) increments and the balloon grew 8.0% of its original length before inflation.

Example 3

The same molding conditions as in the previous examples were used for this example. A 40 mm long 3.0 mm diameter balloon mold was used to make a 100% Pebax 7033 balloon. The formed balloon had a body length of 37.0 mm after the balloon was removed from the mold. The same mold and balloon forming conditions were used for a LCP reinforced Pebax 7033 balloon formed from the melt blend product described in Example 1. The formed balloon had the body length of 38.5 mm, corresponding to a 50% improvement in balloon body length stability as a result of the inclusion of the 5% LCP component.

The foregoing examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A medical device at least a portion of which is composed of a polymeric material in which the polymeric material is a melt blend product of at least two different thermoplastic polymers, one of the thermoplastic polymers being a thermoplastic liquid crystal polymer (LCP) having a melting point of less than 250° C., and another of the thermoplastic polymers being a base polymer, said base polymer is a thermoplastic polyamide elastomer or a thermoplastic polyester elastomer, is present in said melt blend in an amount of from about 85 to about 99.5 weight percent and has a melting point in the range of about 140° C. to about 265° C.; and said LCP is present in an amount of 0.5 to about weight 8 percent.

2. A device as in claim 1 wherein the medical device is a catheter.

3. A device as in claim 2 wherein said device portion is a balloon mounted on the catheter.

4. A device as in claim 1 wherein the base polymer has a melting point of about 220° C. or less.

5. A device as in claim 4 wherein the melting point of the base polymer is from about 150° C. to about 210° C. and the melting point of the LCP is about 150° C. to about 230° C.

* * * * *